US010660258B2

(12) United States Patent
Ide et al.

(10) Patent No.: US 10,660,258 B2
(45) Date of Patent: May 26, 2020

(54) METHOD FOR PRODUCING GERMINATED PLANT SEEDS, A METHOD FOR PRODUCING GERMINATION INDUCTION RAW MATERIAL SEEDS, EXTRACT COMPOSITION OF GERMINATION PROCESSING PLANT SEEDS, AND SCREENING METHOD

(71) Applicant: VEGITABLE PHARMACEUTICAL CO., LTD, Kumamoto, Kumamoto (JP)

(72) Inventors: Hiroyuki Ide, Kumamoto (JP); Tsuyoshi Ide, Kumamoto (JP); Koji Ochiai, Kumamoto (JP)

(73) Assignee: DAIZ ENERGY CO., LTD., Kumamoto (JP)

( * ) Notice: Subject to any disclaimer, the term of this patent is extended or adjusted under 35 U.S.C. 154(b) by 0 days.

(21) Appl. No.: 14/914,463

(22) PCT Filed: Nov. 26, 2015

(86) PCT No.: PCT/JP2015/083196
§ 371 (c)(1),
(2) Date: Feb. 25, 2016

(87) PCT Pub. No.: WO2016/084886
PCT Pub. Date: Jun. 2, 2016

(65) Prior Publication Data
US 2017/0265375 A1    Sep. 21, 2017

(30) Foreign Application Priority Data

Nov. 28, 2014 (JP) ................. 2014-242164

(51) Int. Cl.
| A01C 1/00 | (2006.01) |
| A01G 22/00 | (2018.01) |
| C12P 7/26 | (2006.01) |
| C12P 7/22 | (2006.01) |
| C12P 17/06 | (2006.01) |
| C12P 19/60 | (2006.01) |
| A01G 7/00 | (2006.01) |
| A01G 17/02 | (2006.01) |
| A01N 63/00 | (2020.01) |
| G01N 30/06 | (2006.01) |
| G01N 33/00 | (2006.01) |
| G01N 30/02 | (2006.01) |

(52) U.S. Cl.
CPC ............... *A01C 1/00* (2013.01); *A01G 7/00* (2013.01); *A01G 17/02* (2013.01); *A01G 22/00* (2018.02); *A01N 63/00* (2013.01); *C12P 7/22* (2013.01); *C12P 7/26* (2013.01); *C12P 17/06* (2013.01); *C12P 19/605* (2013.01); *G01N 30/06* (2013.01); *G01N 33/0098* (2013.01); *G01N 2030/027* (2013.01); *G01N 2030/062* (2013.01)

(58) Field of Classification Search
CPC ... A01C 1/00; A01G 7/00; A01G 7/02; A01G 17/02; A01G 22/00; A01N 63/00; C12P 7/22; C12P 7/26; C12P 17/06; C12P 19/605; G01N 30/06; G01N 33/0098; G01N 2030/027; G01N 2030/062
See application file for complete search history.

(56) References Cited

U.S. PATENT DOCUMENTS

| 2001/0031258 A1 | 10/2001 | Nishimura et al. |
| 2008/0003314 A1* | 1/2008 | Ochiai .................. A23L 7/20 424/776 |
| 2008/0008812 A1 | 1/2008 | Ochiai et al. |
| 2012/0082740 A1 | 4/2012 | Collins et al. |

FOREIGN PATENT DOCUMENTS

| JP | 2001322906 A | 11/2001 |
| JP | 2008125515 A | 6/2008 |
| JP | 2010063454 A | 3/2010 |
| JP | 2011200149 A | 10/2011 |
| JP | 2012521746 A | 9/2012 |

OTHER PUBLICATIONS

Fernanda dos Santos Kretzschmar, Marcos Pereira Marinho Aidar, Ione Salgado and Marcia Regina Braga, "Elevated CO2 atmosphere enhances production of defense-related flavonoids in soybean elicited by NO and a fungal elicitor", Environmental and Experimental Botany 65 (2009) 319-329. (Year: 2009).*
Cimmino, A., et al., "Polyphenols as Fungal Phytotoxins, Seed Germination Stimulants and Phytoalexins" Phytochem. Rev., 2013, vol. 12, pp. 653-672.
Dixon, R.A., et al., "Phytoalexins: Enzymology and Molecular Biology", Advances in Enzymology and Related Areas of Molecular Biology, 1983, vol. 55, pp. 1-136.
Notice of Reasons for Rejection issued to Japanese Application No. 2014-242164; dated Mar. 10, 2015.
Pedras, M.S.C., et al., "Metabolic Changes in Roots of the Oilseed Canola Infected with the Biotroph Plasmodiophora brassicae: Phytoalexins and Phytoanticipins", Journal of Agricultural and Food Chemistry, 2008, vol. 56, pp. 9949-9961.

(Continued)

*Primary Examiner* — Mina Haghighatian
*Assistant Examiner* — Nathan W Schlientz
(74) *Attorney, Agent, or Firm* — Cantor Colburn LLP

(57) ABSTRACT

The present invention provides a novel method of manufacturing germinated plant seeds suitable for producing a large amount of phytoalexin, a method of manufacturing raw material seeds for germination induction for use in manufacture of the above germinated plant seeds, an extract composition of the germinated plant seeds and a screening method for a plant seed candidate for use in producing a target substance. The method of manufacturing raw material seeds for germination induction comprises a pre-treatment step of maintaining plant seeds under atmosphere conditions of a carbon dioxide concentration of 400 ppm or more and/or an oxygen concentration of 19 vol % or less continuously for 5 hours or more.

15 Claims, 8 Drawing Sheets

(56) References Cited

OTHER PUBLICATIONS

Simons, R., et al., "Increasing Soy Isoflavonoid Content and Diversity by Simultaneous Malting and Challenging by a Fungus to Modulate Estrogenicity" Journal of Agricultural and Food Chemistry, 2011, vol. 59, pp. 6748-6758.

Wu, Z., et al., "Food Grade Fungal Stress on Germinating Peanut Seeds Induced Phytoalexins and Enhanced Polyphenolic Antioxidants", Journal of Agricultural and Food Chemistry, 2011, vol. 59, pp. 5993-6003.

* cited by examiner

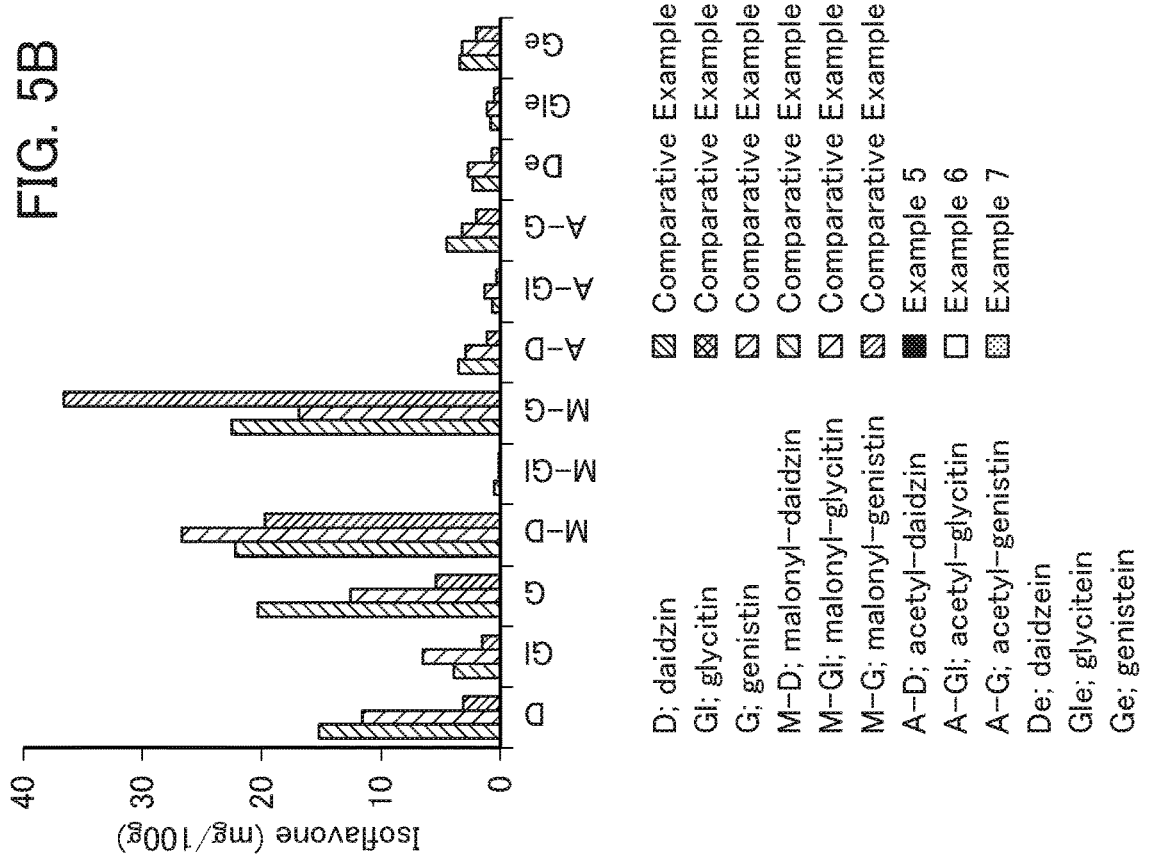
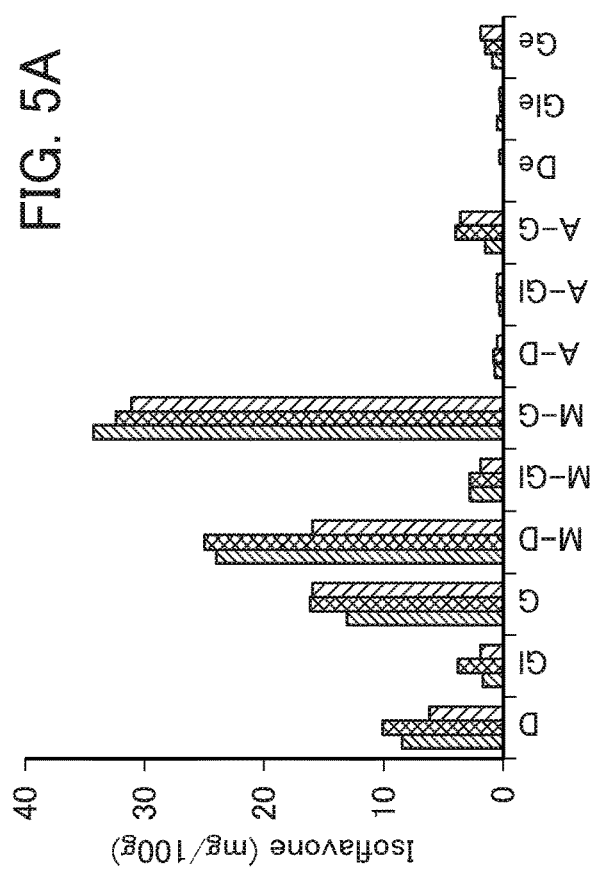
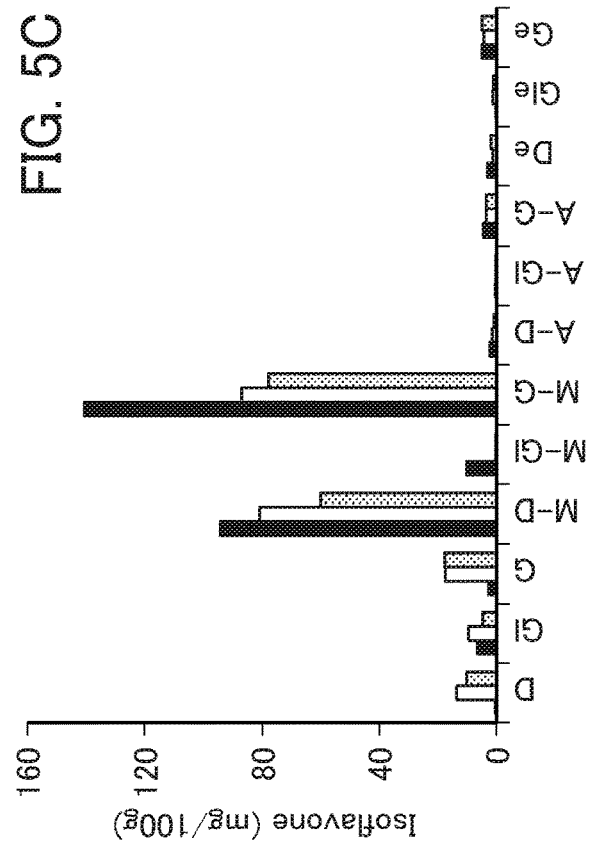

METHOD FOR PRODUCING GERMINATED PLANT SEEDS, A METHOD FOR PRODUCING GERMINATION INDUCTION RAW MATERIAL SEEDS, EXTRACT COMPOSITION OF GERMINATION PROCESSING PLANT SEEDS, AND SCREENING METHOD

This is the U.S. national stage of application No. PCT/JP2015/083196, filed on Nov. 26, 2015. Priority under 35 U.S.C. § 119(a) and 35 U.S.C. § 365(b) is claimed from Japanese Application No. 2014-242164, filed Nov. 28, 2014, the disclosure of which is also incorporated herein by reference.

TECHNICAL FIELD

The present invention relates to a method of manufacturing germinated plant seeds, a method of manufacturing raw material seeds for germination induction, an extract composition of germinated plant seeds, and a screening method.

BACKGROUND ART

Plants are known to produce useful compounds such as phytochemicals during metabolic activities. Phytochemicals can be used in pharmaceutical products and health foods. Further, plant metabolism depends on growth environments of the plant. Therefore, the types and amounts of compounds produced in the course of the plant metabolism are thought to be changed by altering environment factors related to the growth of the plant. Accordingly, studies have been traditionally conducted for allowing plants to produce useful compounds such as phytochemicals by changing environmental factors related to the growth of the plants.

As phytochemicals, for example, polyphenol is known. Patent Document 1 discloses a method of manufacturing germinated plant seeds, comprising maintaining plant seeds under atmosphere conditions of a carbon dioxide concentration of 2000 ppm or more and/or an oxygen concentration of 18 vol % or less and further maintaining the plant seeds at a temperature within the range of the germination temperatures, wherein the amount of a readily water-soluble polyphenol is increased.

Patent Document 1: Japanese Unexamined Patent Application, Publication No. 2008-125515

DISCLOSURE OF THE INVENTION

Problems to be Solved by the Invention

Meanwhile, phytoalexin is a secondary metabolite which common plants do not produce, and known to have an efficacy for a biological function. However, the method of manufacturing germinated plant seeds according to Patent Document 1 merely increases the amount of a readily water-soluble polyphenol, but can not produce a sufficient amount of phytoalexin.

The present invention is made in view of the above situation. An objective of the present invention is to provide a novel method of manufacturing germinated plant seeds suitable for producing a large amount of phytoalexin. Another objective of the present invention is to provide a method of manufacturing raw material seeds for germination induction for use in manufacture of the above germinated plant seeds. Further, another objective of the present invention is to provide an extract composition of the germinated plant seeds. Yet another objective of the present invention is to provide a screening method for a plant seed candidate for use in production of a target substance.

Means for Solving the Problems

The present inventors find that a large amount of phytoalexin can be produced in germinated plant seeds by subjecting plant seeds to a pre-treatment of controlling germination environments, and then inoculating the plant seeds with a microbial pathogen. Then the present invention is completed. More specifically, the present invention provides the following.

(1) A method of manufacturing raw material seeds for germination induction, comprising a pre-treatment step of maintaining plant seeds under atmosphere conditions of a carbon dioxide concentration of 400 ppm or more and/or an oxygen concentration of 19 vol % or less continuously for 5 hours or more.

(2) The method of manufacturing raw material seeds for germination induction according to (1), wherein the maintenance for 5 hours or more is not performed by immersing the plant seeds.

(3) The method of manufacturing raw material seeds for germination induction according to (1) or (2), wherein the pre-treatment comprises performing a combination of the maintenance for 5 hours or more and the termination of the maintenance for 2 times or more.

(4) The method of manufacturing raw material seeds for germination induction, comprising a pre-treatment step of treating plant seeds so that the mass of a phytochemical in the plant seeds, after the pre-treatment step, is from 2 times to 100 times relative to the mass of the phytochemical in the plant seeds before the pre-treatment step.

(5) The method of manufacturing raw material seeds for germination induction according to (4), wherein the pre-treatment step comprises treating the plant seeds so that the mass of the entire phytochemicals in the plant seeds after the pre-treatment step is from 2 times to 100 times relative to the mass of the entire phytochemicals in the plant seeds before the pre-treatment step.

(6) The method of manufacturing raw material seeds for germination induction according to any one of (1) to (5), wherein the pre-treatment step is performed so that the mass of glutamic acid in the plant seeds after the pre-treatment step is 2.5 times or more relative to the mass of glutamic acid in the plant seeds before the pre-treatment step.

(7) A method of manufacturing raw material seeds for germination induction, comprising a pre-treatment step of treating plant seeds so that the mass of a phytochemical in the plant seeds after the pre-treatment step is 2 times or more relative to the mass of the phytochemical in the plant seeds before the pre-treatment step, wherein the pre-treatment step is performed so that the mass of glutamic acid in the plant seeds after the pre-treatment step is 2.5 times or more relative to the mass of glutamic acid in the plant seeds before the pre-treatment step.

(8) The method of manufacturing raw material seeds for germination induction according to any one of (1) to (7), wherein the phytochemical content in the plant seeds before the pre-treatment step is 0.1 mg/g or more.

(9) The method of manufacturing raw material seeds for germination induction according to (8), wherein the plant seeds are those of Vitaceae, Leguminosae, Solanaceae, Lamiaceae or Cruciferae.

(10) A method of manufacturing germinated plant seeds, comprising a germination induction step of inoculating the raw material seeds for germination induction according to any one of (1) to (9) with a microbial pathogen, and placing the raw material seeds for germination induction in an environment where germination is inducible and the pathogen is viable.

(11) The method of manufacturing germinated plant seeds according to (10), wherein the pathogen is an edible microorganism.

(12) An extract composition of the germinated plant seeds manufactured by the method according to (10) or (11).

(13) A screening method for a plant seed candidate for use in producing a target substance, comprising:

a pre-treatment step of maintaining test plant seeds under atmosphere conditions of a carbon dioxide concentration of 400 ppm or more and/or an oxygen concentration of 19 vol % or more continuously for 5 hours or more, a germination induction step of inoculating the test plant seeds with a microbial pathogen after the pre-treatment step, and placing the test plant seeds under an environment in which germination is inducible and the pathogen is viable, a step of detecting the target substance in the test plant seeds after the germination induction step, and a step of selecting a plant seed candidate for use in producing the target substance based on the detection results.

(14) The screening method according to (13), wherein the maintenance for 5 hours or more is not performed by immersing the test plant seeds.

(15) The screening method according to (13) or (14), wherein the pre-treatment step comprises performing a combination of the maintenance for 5 hours or more and the termination of the maintenance for 2 times or more.

(16) A screening method for a plant seed candidate for use in producing a target substance, comprising:

a pre-treatment step of treating test plant seeds so that the mass of a phytochemical in the test plant seeds after the pre-treatment step is from 2 times to 100 times relative to the mass of the phytochemical in the test plant seeds before the pre-treatment step, a germination induction step of inoculating the test plant seeds with a microbial pathogen after the pre-treatment step, and placing the test plant seeds under an environment in which germination is inducible and the pathogen is viable, a step of detecting the target substance in the test plant seeds after the germination induction step, and a step of selecting a plant seed candidate for use in producing the target substance based on the detection results.

(17) The screening method according to (16), wherein the pre-treatment step comprises treating the test plant seeds so that the mass of the entire phytochemicals in the test plant seeds after the pre-treatment step is from 2 times to 100 times relative to the mass of the entire phytochemicals in the test plant seeds before the pre-treatment step.

(18) The screening method according to any one of (13) to (17), wherein the pre-treatment step is performed so that the mass of glutamic acid in the test plant seeds after the pre-treatment step is 2.5 times or more relative to the mass of glutamic acid in the test plant seeds before the pre-treatment step.

(19) A screening method for a plant seed candidate for use in producing a target substance, comprising:

a pre-treatment step of treating test plant seeds so that the mass of a phytochemical in the test plant seeds after the pre-treatment step is 2 times or more relative to the mass of the phytochemical in the test plant seeds before the pre-treatment step, a germination induction step of inoculating the test plant seeds with a microbial pathogen after the pre-treatment step, and placing the test plant seeds under an environment in which germination is inducible and the pathogen is viable, a step of detecting the target substance in the test plant seeds after the germination induction step, and a step of selecting a plant seed candidate for use in producing the target substance based on the detection results, wherein the pre-treatment step is performed so that the mass of glutamic acid in the test plant seeds after the pre-treatment step is 2.5 times or more relative to the mass of glutamic acid in the test plant seeds before the pre-treatment step.

Effects of the Invention

The present invention can provide a novel method of manufacturing germinated plant seeds suitable for producing a large amount of phytoalexin; a method of manufacturing raw material seeds for germination induction used for manufacture of the above germinated plant seeds; an extract composition of the germinated plant seeds; and a screening method for a plant seed candidate for use in producing a target substance.

BRIEF DESCRIPTION OF THE DRAWINGS

FIG. 5 shows: (FIG. 5A) a graph illustrating the amounts of various types of isoflavone as phytochemicals in the compositions extracted from the soybean according to Comparative Examples 4 to 6; (FIG. 5B) a graph illustrating the amounts of various types of isoflavone as phytochemicals in the compositions extracted from the soybean according to Comparative Examples 7 to 9; (FIG. 5C) a graph illustrating the amounts of various types of isoflavone as phytochemicals in the compositions extracted from the raw material seeds for germination induction according to Examples 5 to 7.

PREFERRED MODE FOR CARRYING OUT THE INVENTION

Figure 1A:
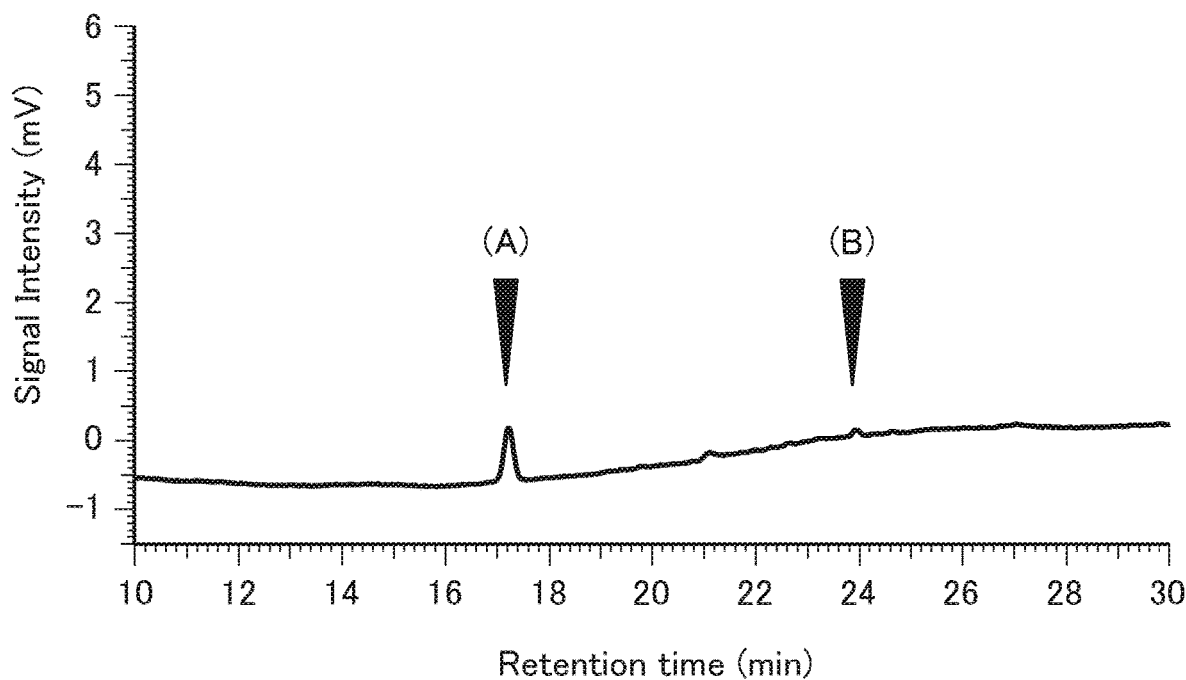
FIG. 1 shows analysis results from high performance liquid chromatography of (FIG. 1A) an extract composition of the grape seeds according to Comparative Example 1 and (FIG. 1B) an extract composition of the germinated plant seeds according to Example 1.

Below, specific embodiments of the present invention will be described in detail. The present invention is, however, not limited to the following embodiments in any sense, and appropriate modifications may be made for implementation without departing from the scope and sprit of the present invention.

<Method of Manufacturing Raw Material Seeds for Germination Induction>

The method of manufacturing raw material seeds for germination induction according to the present invention compromises a pre-treatment step of maintaining plant seeds under atmosphere conditions of a carbon dioxide concentration of 400 ppm or more and/or an oxygen concentration of 19 vol % or less continuously for 5 hours or more, or a pre-treatment step of treating plant seeds so that the mass of a phytochemical in the plant seeds after the pre-treatment step is 2 times or more relative to the mass of the phytochemical in the plant seeds before the pre-treatment step.

(Pre-Treatment Step)

The pre-treatment step in the method of manufacturing raw material seeds for germination induction according to the present invention is a step comprising a pre-treatment step of maintaining plant seeds under atmosphere conditions of a carbon dioxide concentration of 400 ppm or more and/or an oxygen concentration of 19 vol % or less continuously for 5 hours or more, or a pre-treatment step of treating plant seeds so that the mass of a phytochemical in the plant seeds after the pre-treatment step is 2 times or more relative to the mass of the phytochemical in the plant seeds before the pre-treatment step. As used in the present invention, the term "raw material seeds for germination induction" refer to seeds which are used as primarily a raw material for manufacturing germinated plant seeds as described below, and in which the amount of a phytochemical is increased by the pre-treatment step.

As used in the present invention, the term "pre-treatment" refers to a process performed in the preceding stage of the germination induction step in the method of manufacturing germinated plant seeds described below, in which the amount of a phytochemical in the seeds is increased. Since the amount of a phytochemical is increased as described above, manufactured raw material seeds for germination induction can produce a large amount of phytoalexin due to the germination induction step in the method of manufacturing raw material seeds for germination induction described below. Note that germination induction is performed in the method of manufacturing germinated plant seeds described below, but germination induction may also be performed in the "pre-treatment" according to the present invention.

Further, the production amount of amino acids, carbohydrates and the like in plant seeds can also be increased due to the pre-treatment step according to the present invention. This can be presumably explained as follows: plant seeds are heterotrophic immediately after germination, and require nutrients for growing into autotrophs, which can perform photosynthesis. Therefore, plant seeds decompose proteins stored therein into amino acids for use as nitrogen sources, and also decompose starch stored therein into carbohydrates for use as carbon sources. As a consequence that a large amount of amino acids and carbohydrates are produced in plant seeds as described above, the production amount of phytoalexin is increased in the method of manufacturing germinated plant seeds described below.

The pre-treatment can be performed by maintaining plant seeds under atmosphere conditions of a carbon dioxide concentration of 400 ppm or more and/or an oxygen concentration of 19 vol % or less continuously for 5 hours or more. The carbon dioxide concentration and/or the oxygen concentration were also controlled in the aforementioned method according to Patent Document 1. However, they were maintained intermittently, and the continuous holding time was short, merely showing an increase in the amount of a readily water-soluble polyphenol. In contrast, in the present invention, plant seeds are maintained under the aforementioned atmosphere for as long as 5 hours or more, thereby the amount of a phytochemical in the seeds can be increased significantly.

There is no particular limitation for the continuous holding time at a carbon dioxide concentration and/or an oxygen concentration as long as it is longer than 5 hours, but it is preferably 6 hours or more, more preferably 6.5 hours or more, even more preferably 7 hours or more, yet even more preferably 8 hours or more, still more preferably 10 hours or more, and most preferably 12 hours or more in view of promoting an increase in the production amount of phytochemicals in the seeds. On the other hand, in a case where the holding time is too long, the amount of a phytochemical becomes too large, and the microbial pathogen will be less tolerant to the phytochemical in the method of manufacturing germinated plant seeds described below, resulting in decreasing the production amount of phytoalexin. Considering these, the holding time is preferably 72 hours or less, more preferably 48 hours or less, and more preferably 36 hours or less.

There is no particular limitation for the carbon dioxide concentration, but in view of promoting phytochemical production in the seeds, it is preferably 2000 ppm or more, more preferably 5000 ppm or more, even more preferably 10000 ppm or more, and most preferably 20000 ppm or more. Further, there is no particular limitation for the upper limit of the carbon dioxide concentration, but it is preferably 100000 ppm or less, more preferably 75000 ppm or less, even more preferably 50000 ppm or less, and most preferably 35000 ppm or less. This is because in a case where it is too high, the oxygen concentration is consequently decreased to promote anaerobic respiration in plant seeds, resulting in a decreased phytochemical production in the seeds.

There is no particular limitation for the oxygen concentration, but in view of promoting phytochemical production in the seeds, it is preferably 18 vol % or less, more preferably 15 vol % or less, even more preferably 12 vol % or less, and most preferably 9 vol % or less. Further, there is no particular limitation for the lower limit of oxygen, but it is preferably 3 vol % or more, more preferably 4 vol % or more, even more preferably 6 vol % or more, and most preferably 7 vol % or more. This is because in a case where it is too low, anaerobic respiration is promoted in plant seeds, resulting in a decreased phytochemical production in the seeds.

There is no particular limitation for the manner of maintaining a carbon dioxide concentration and an oxygen concentration, but it may be performed as follows: plant seeds may be deposited in a sealable or partly sealable container to reduce the oxygen concentration around the plant seeds, thereby increasing the carbon dioxide concentration. Therefore, by maintaining such a state, the carbon dioxide concentration and the oxygen concentration can be maintained within the desired atmosphere conditions. The maintenance may be terminated, for example, by releasing the seal or by watering. Further, the carbon dioxide concentration and the oxygen concentration to be maintained can be adjusted by the degree of container sealing and the extent of seed deposition.

In the present invention, once the aforementioned maintenance is terminated, plant seeds may again be maintained under atmosphere conditions of a carbon dioxide concentration of 400 ppm or more and/or an oxygen concentration of 19 vol % or less continuously for 5 hours or more. In the present invention, there is no particular limitation for the number of times to perform the maintenance and the termination thereof. For example, it may be 1 time or more (such as 2 times or more, 3 times or more, 4 times or more, 5 times or more, 6 times or more, 8 times or more, 9 times or more), and it may be 10 times or less (such as 9 times or less, 8 times or less, 7 times or less, 6 times or less, 5 times or less, 4 times or less, 3 times or less, 2 times or less), but it is preferably 1 to 10 times, more preferably 2 to 8 times, even more preferably 4 to 6 times.

In the present invention, the carbon dioxide concentration and the oxygen concentration are measured with a Gastec indicating tube under conditions of indication accuracy: CV=5% (CV: Coefficient of Variation=σ: standard deviation/mean-value×100).

Germination-potent seeds are preferably used for the plant seeds in the present invention. The germination-potent seeds refer to those which are not in a dormant state. Note that in a case where dormant seeds are used, they are subjected to heating, watering and the like before the pre-treatment step such that they come out of the dormant state to become germination-potent, thereby allowing the seeds to be used in the pre-treatment step.

In the present invention, the pre-treatment for increasing the amount of a phytochemical in seeds can be performed by maintaining plant seeds under atmosphere conditions of a carbon dioxide concentration of 400 ppm or more and/or an oxygen concentration of 19 vol % or less continuously for 5 hours or more. However, the pre-treatment may not be limited to this, and any methods may be used as long as the mass of a phytochemical in the plant seeds after the pre-treatment step is, for example, 2 times or more relative to the mass of the phytochemical in the plant seeds before the pre-treatment step. Note that the treatment may be performed so that the mass of at least one or more phytochemicals is 2 times or more or the mass of the entire phytochemicals is 2 times or more.

There is no particular limitation for the plant treatment of increasing the mass of a phytochemical by 2 times or more. In addition to a method of adjusting and holding atmosphere conditions of a carbon dioxide concentration and/or an oxygen concentration as described above, the treatment may be performed by controlling an environmental factor involved in germination of seeds such as the temperature around seeds, water, light, plant hormones, pH in seeds, ion concentrations, microorganism, microorganism signals alone or in combination. Further, it may also be performed by combining controlling these environmental factors and controlling a carbon dioxide concentration and/or an oxygen concentration.

There is no particular limitation for the temperature, but the treatment may be performed, for example, at 10 to 45° C. However, in view of promoting an increased phytochemical in seeds, it is preferably 15 to 40° C., more preferably 20 to 35° C. or more, and even more preferably 25 to 35° C. The adjustment of temperature can also be performed by any conventionally known methods, but it may be performed by means of, for example, a temperature-adjustable incubator, a room-temperature adjustable cultivation room, a heater, a cooling device, an air controller, watering and the like. There is no particular limitation for the period of maintaining temperature under desired conditions. The period may appropriately be set depending on, for example, other environmental factors such as the concentration of carbon dioxide.

The control of water can be performed, for example, by watering. In the present invention, there is no particular limitation for the operation of watering, but it may be performed, for example, by spraying water or pouring water on seeds, or either by immersing plant seeds into water or not immersing the plant seeds into water. Further, in the present invention, humidity, temperature, carbon dioxide concentration, oxygen and the like around seeds can be adjusted by controlling water, thereby increasing the amount of a phytochemical in seeds. The control of water can be performed by appropriately selecting the holing time, the number of times of watering and the like, depending on humidity, temperature, a carbon dioxide concentration, oxygen and the like.

A microbicide may be contained in water at an amount of, for example, 10 ppm or more. However, in a case where a microorganism is used in the pre-treatment, use of a large amount of a microbicide is not recommended because it may interfere with the microbial growth in the method of manufacturing germinated plant seeds described below. In this case, the concentration of a microbicide is preferably 9 ppm or less, more preferably less than 8 ppm, and even more preferably less than 5 ppm. Any conventional known microbicides can be used, including, for example, sodium hypochlorite and the like.

The control of light may be performed, without particular limitation, by emitting light with a light intensity of, for example, 5 to 1000 μmol/m/day. Further, there is no particular limitation for the irradiation time of light, but it is preferably 0.5 to 24 hours/day, and more preferably 6 to 12 hours/day. In order to perform irradiation with light, any conventionally known methods can be used such as a fluorescent lamp.

The control of plant hormones may be performed, without particular limitation, with ethylene gas ($C_2H_4$), gibberellin and the like, for example. Plant hormones to be controlled include, for example, auxin, gibberellin, cytokinin, abscisic acid, ethylene, brassinosteroid, jasmone acids, florigene, strigolactone and the like.

The control of pH may be performed, without particular limitation, by controlling pH to 2.3 to 9.0. Any conventional known means can be used for the method of controlling pH.

The control of an ion concentration may be performed, without particular limitation, by adjusting ions (for example, $K^+$, $Mg^{2+}$, $Ca^{2-}$, $Na^+$ and the like) in water with which seeds are watered to 0.001 ppm to 100 ppm, for example.

The control of a microorganism or a microorganism signal may be performed, without particular limitation, for example, by controlling a microorganism such as Aspergillus oryzae or a microorganism signal such as β glucan.

In a case where the amount of a phytochemical increased by the pre-treatment is larger, the production of a larger amount of phytoalexin will be promoted through an interaction with a pathogen in the method of manufacturing germinated plant seeds as described below. In view of these, plant seeds are preferably treated so that the mass of a phytochemical in the plant seeds after the pre-treatment step is 5 times or more, more preferably 10 times or more, and even more preferably 20 times or more relative to the mass of the phytochemical in the plant seeds before the pre-treatment step. On the other hand, in a case where a phytochemical is increased too much, a pathogen will be less viable, and thus phytoalexin will be difficult to be produced in a large quantity in the method of manufacturing germinated plant seeds as described below. In view of these, plant seeds are preferably treated so that the mass of a phytochemical in the plant seeds after the pre-treatment step is 100 times or less, more preferably 80 times or less, and even more preferably 60 times or less relative to the mass of the phytochemical in the plant seeds before the pre-treatment step.

In the present invention, there is no particular limitation for the plant seeds to be used, and they include seeds of, for example, Vitaceae (Cabernet Sauvignon, Pinot Noir and the like), Leguminosae (*Glycine max, Trifolium pratense* and the like), Solanaceae Compositae (*Lycopersicon esculentum* (Red pair and the like) and the like), Asteraceae, Cruciferae, Lamiaceae, Poncirus, Rosaceae, Ginkgoaceae, Poaceae, Moraceae, Polygonaceae, Theaceae, Oleaceae, Osmanthus heterophyllus, Cucurbitaceae, Punicaceae and the like. More specifically, they include grape, sunflower, Cabernet Sauvignon, clover, *Brassica*, sesame, perilla, linseed, *Perilla frutescens*, peanut, rice, buckwheat, cone, wheat, wild rice, barley, foxtail millet, Barnyard millet, fenugreek, rosemary, thyme, sage, mint, American red cherry, apricot, almond, grapefruit, orange, plum, St. John's wort, tomato, strawberry, carrot, bell pepper, mangosteen, mango, loquat, burdock, cacao and the like. In a case where the phytochemical content in plant seeds is higher, the production amount of phytoalexin is increased in the method of manufacturing germinated plant seeds as described below. Therefore, plant seeds having a higher phytochemical content are preferably used. In this regard, as plant seeds before the pre-treatment, preferably used are those having a phytochemical content of 1 mg/g or more, more preferably 2 mg/g or more, even more preferably 4 mg/g or more, and most preferably 8 mg/g or more. More specifically, among those, seeds of Vitaceae, Leguminosae, Solanaceae, Cruciferae are preferred in view of large seed sizes and higher phytochemical contents. They are also preferred in view of availability at relatively low cost. In particular, seeds of grape and tomato are preferred in view of effective use of untapped natural resources because of residues generated upon manufacture of wine, tomato juice and the like.

The term "phytochemical" as used in the present invention refers to at least one or more phytochemicals. There is no particular limitation for the phytochemicals as long as they are conventionally known phytochemicals, including, but not limited to, for example, polyphenols such as isoflavone, terpenoids such as lycopene, long alkylphenol derives such as capsaicin, carbohydrate-related compounds such as saponin, organosulfur compounds such as sulforaphane. Among these phytochemicals, the amount of isoflavone is preferably increased in the pre-treatment according to the present invention because the production amount of phytoalexin is increased in the method of manufacturing germinated seeds. Note that the term "isoflavone" as used in the present invention refers to isoflavones which are flavonoids having isoflavone as the backbone structure. Further, in the present invention, a phytochemical can be phytoalexin.

In the present invention, the mass of a phytochemical in seeds is measured by high performance liquid chromatography.

According to the pre-treatment step in the present invention, nutrients for a microbial pathogen described below such as amino acids and carbohydrates can be produced in the seeds. As a consequence that amino acids and carbohydrates are produced in large quantities as described above, a large production amount can be achieved in the method of manufacturing germinated plant seeds as described below. There is no particular limitation for the amino acid as long as it serves as a plant nutrient. In particular, the amount of glutamic acid is preferably increased after the pre-treatment by 2.5 times or more (3 times or more, 3.5 times or more and the like) in the mass ratio. Further, the amount of carbohydrates is preferably increased by 2.5 times or more relative to that before the pre-treatment. In a case where the contents of amino acids and carbohydrates are increased as described above, a microbial pathogen is more viable, allowing the amount of a phytochemical to be significantly increased by the pre-treatment in the method of manufacturing germinated plant seeds as described below. For example, when the amount of glutamic acid as an amino acid is 2.5 times or more in terms of its content relative to that before the pre-treatment, the amount of a phytochemical can be increased up to 30 times or less (25 times or less, 20 times or less and the like) relative to that before the pre-treatment.

In the present invention, amino acids are measured by UHPLC. Further, carbohydrates are measured by HPLC.

<Method of Manufacturing Germinated Plant Seeds>

The method of manufacturing germinated plant seeds according to the present invention comprises a germination induction step of inoculating the above raw material seeds for germination induction with a microbial pathogen, and placing the raw material seeds for germination induction under an environment in which germination is inducible and the pathogen is viable.

(Germination Induction Step)

The germination induction step in the method of manufacturing germinated plant seeds according to the present invention is a step of placing raw material seeds for germination induction under an environment in which germination is inducible and a pathogen is viable. According to the present invention, germinated plant seeds capable of producing a large amount of phytoalexin can be manufactured through this step.

Conventionally, a method is known for producing phytoalexin such as isoflavones by preparing germinated plant seeds using a pathogen (see Simons R, Vincken J P, Roidos N, Bovee T F, van Iersel M, Verbruggen M A, Gruppen H. Increasing Soy Isoflavonoid Content and Diversity by Simultaneous Malting and Challenging by a Fungus to Modulate Estrogenicity. J. Agric. Food Chem., 2011, 59 (12), pp 6748-6758). However, according to the conventional method, the period of time after inoculation with a pathogen is as long as 9 days, causing problems such as cost and bacteria management. Therefore, it is not practical. However, according to the present invention, a large amount of phytoalexin can be produced in a short time after inoculation with a microorganism, which is less than 9 days (for example, 1 to 5 days).

The above raw material seeds for germination induction subjected to the pre-treatment according to the present invention produce a large amount of a phytochemical which serves as a raw material for phytoalexin. Since the amount of a phytochemical is high as described above, seeds are less susceptible to decomposition even with the inoculation of a microbial pathogen, and as a result, can potentially produce phytoalexin for a prolonged period of time. Therefore, a large amount of phytoalexin can be produced.

As described above, amino acids and carbohydrates as nutrients are produced in large quantities in the seeds by performing the pre-treatment according to the present invention. Since a pathogen can be more tolerant to a phytochemical due to the nutrients, the pathogen is viable for a prolonged period of time in the presence of a large amount of the phytochemical after inoculation with the pathogen. Further, this can presumably be explained as follows: the raw material seeds for germination induction after the pre-treatment remain under germination potent conditions during that time. As a result of this, a mutual stimulation arises between the raw material seeds for germination induction after the pre-treatment and the pathogen. Consequently, phytoalexin is efficiently produced in the seeds.

There is no particular limitation for the period of time of placing seeds under the above environment after inoculation with a pathogen, but it may be, for example, 6 hours to 7 days and the like. However, it is preferably 5 days or less, and more preferably 4 days or less because the plant may become susceptible to decomposition when placed for too long. However, in a case where the amounts of amino acids and carbohydrates are increased in the seeds as described above, a pathogen is viable for a prolonged period of time. Therefore, the raw material seeds for germination induction can be placed under the above environment for a long time after inoculation with the pathogen. The period of time of placing seeds under the above environment after inoculation with a pathogen may be determined based on how much the amount of phytoalexin in the seeds before inoculation is increased. For example, seeds may be placed under the above environment until the mass of phytoalexin in the seeds before inoculation becomes 1 mg/g or more (such as 5 mg/g or more, 10 mg/g or more, 15 mg/g or more, 20 mg/g or more, 25 mg/g or more, 30 mg/g or more). Note that in this case, seeds may be placed under the above environment so that the mass of at least one or more types of phytoalexin is 1 mg/g or more and the like, or so that the mass of the entire types of phytoalexin is 1 mg/g or more and the like.

In the present invention, the mass of phytoalexin in the seeds is measured with a quadrupole mass spectrometer LC/MS/MS.

The conditions for LC are as follows.

Column: an AQCUITY UPLC BEH Shield RP18 Column (1.7 μm, 2.1 mm.×150 mm), an AQCUITY UPLC BEH Shield RP18 VanGuard Pre-Column (1.7 μm, 2.1 mm.×5 mm)

The term phytoalexin as used in the present invention refers to at least one or more types of phytoalexin. Types of phytoalexin which can be produced vary depending on species of seeds. For example, in a case where grape seeds are used, stilbenes such as piceid and resveratrol can be produced. In a case where soybean is used, various glyceollins (such as Glyceollin I, Glyceollin II, Glyceollin III, Glyceollin IV) can be produced.

As used in the present invention, the term "pathogen" generally refers to a so-called plant pathogen, which is used to allow seeds to produce phytoalexin according to the present invention. There is no particular limitation for the pathogen in the present invention as long as it is a microorganism. A person skilled in the art can select an appropriate pathogen depending on the seeds. In particular, the pathogen is preferably an edible microorganism. There is no particular limitation for the edible microorganisms, and they include, for example, Tempeh fungus, Koji mold, *Bacillus subtilis* var natto, yeast, lactic acid bacteria, mushroom and the like. Among these, Tempeh fungus, Koji mold, *Bacillus subtilis* var natto, yeast, lactic acid bacteria are preferred, and Tempeh fungus, Koji mold, yeast, lactic acid bacteria are more preferred.

In the present invention, inoculation with a pathogen can be performed by the conventionally known methods.

In the present invention, there is no particular limitation for the environment in which germination of the raw material seeds for germination induction can be induced, and a pathogen is viable, and it can be appropriately selected depending on the seeds and pathogens.

For example, the environment may be of conditions similar to those selected from the conditions used in the above pre-treatment step, but among these conditions, those in which germination is inducible, and a pathogen is viable need to be selected. The germination-inducible environments include, for example, those of a carbon dioxide concentration of 300 to 120000 ppm and an oxygen concentration of 5 to 20 vol %, a temperature of 10 to 45° C. and the like. The environment is selected from these, considering a carbon dioxide concentration, an oxygen concentration and a temperature required for the pathogen. For example, in a case where the pathogen is an anaerobic microorganism, a lower oxygen concentration is preferred. In a case where it is aerobic microorganism, a higher oxygen concentration is preferred.

<Extract Composition>

The extract composition according to the present invention is an extract composition of the above raw material seeds for germination induction.

There is no particular limitation for the method of preparing the extract composition of the present invention, and any conventionally known methods can be used. However, preparation may be performed, for example, by adding water and an organic solvent (such as ethanol) to a container having a raw material for germination induction, and then grinding the content. Further, a step of further purifying, isolating a useful material such as phytoalexin may be provided.

There is no particular limitation for the use of the extract composition of the present invention. The extract composition of the present invention can contain a useful compound such as phytoalexin, and in such a case, it may be suitable for use in health foods, pharmaceutical products and the like after preparation.

<Screening Method>

The screening method according to the present invention is a screening method for a plant seed candidate for use in producing a target substance, comprising: a pre-treatment step of maintaining test plant seeds under atmosphere conditions of a carbon dioxide concentration of 400 ppm or more and/or an oxygen concentration of 19 vol % or more continuously for 5 hours or more, or a pre-treatment step of treating test plant seeds so that the mass of a phytochemical in the test plant seeds after the pre-treatment step is 2 times or more relative to the mass of the phytochemical in the test plant seeds before the pre-treatment step, a germination induction step of inoculating the test plant seeds with a microbial pathogen after the pre-treatment step, and placing raw material seeds for germination induction under an environment in which germination is inducible, and the pathogen is viable, a step of detecting the target substance in the test plant seeds after the germination induction step, and a step of selecting the plant seed candidate for use in producing the target substance based on the detection results, if detected.

According to the method of manufacturing raw material seeds for germination induction and the method of manufacturing germinated plant seeds as described above, a large mount of phytoalexin can be obtained, but the types of phytoalexin obtained vary depending on the plant species. Therefore, in a case where a useful compound such as a specific type of phytoalexin is desired, whether the desired compound is produced or not in a certain species of seeds can be determined by using the method of manufacturing raw material seeds for germination induction and the method of manufacturing germinated plant seeds as described above. That is, a plant seed candidate which can be used to produce a target substance can be screened for by using the method of manufacturing raw material seeds for germination induction and the method of manufacturing germinated plant seeds as described above.

In the present invention, there is no particular limitation for the target substance, but for example, a secondary metabolite such as phytoalexin is suitable as a target substance for the screening method of the present invention. There is also no particular limitation for the types of phytoalexin, and any of those conventionally known may be used.

(Pre-Treatment Step)

The pre-treatment step in the screening method according to the present invention is a pre-treatment step of maintaining test plant seeds under atmosphere conditions of a carbon dioxide concentration of 400 ppm or more and/or an oxygen concentration of 19 vol % or more continuously for 5 hours or more, or a pre-treatment step of treating test plant seeds so that the mass of a phytochemical in the test plant seeds after the pre-treatment step is 2 times or more relative to the mass of the phytochemical in the test plant seeds before the pre-treatment step. Those similar to the pre-treatment step in the method of manufacturing raw material seeds for germination induction described above may be used as the above pre-treatment step.

There is no particular limitation for the test plant seeds, and any conventionally known plant seeds may be selected suitably depending on the objective. However, germination-potent seeds and the like are preferred.

As described above, nutrients for a microbial pathogen such as amino acids and carbohydrates can be produced in the seeds according to the pre-treatment step of the present invention. Therefore, test plant seeds capable of producing amino acids, carbohydrates and the like in large quantities after the pre-treatment step is suitable for producing a useful compound such as phytoalexin in the subsequent germination induction step. Therefore, the screening method according to the present invention may comprise a step of determining the amounts of amino acids and carbohydrates in the test plant seeds after the pre-treatment step. In particular, it is preferred to determine whether the amount of glutamic acid, among amino acids, is increased due to the pre-treatment step by 2.5 times or more (3 times or more, 3.5 times or more and the like) in the mass ratio after the pre-treatment.

(Germination Induction Step)

Those similar to the germination induction step in the method of manufacturing germinated plant seeds described above can be used for the germination induction step in the screening method according to the present invention.

(Detection Step)

The germination induction step in the screening method according to the present invention is a step of detecting a target substance in the test plant seeds after the germination induction step.

Any conventionally known detection methods can be used for the detection. For example, test plant seeds may be ground to prepare an extract composition, which may be subjected to detection by high performance liquid chromatography.

(Selection Step)

The selection step is a step for selecting a plant seed candidate for use in producing a target substance after the above detection step based on the detection results if detected.

There is no particular limitation for the selection method, and a candidate substance may be selected by any conventionally known selection methods. For example, test plant seeds may be selected as a plant seed candidate by determining, from the above detection results, that the target substance has been produced. Alternatively, selection may be made by comparison with the amount of the target substance in other plant seeds. Specific examples of a comparison reference may include, for example, plant seeds of the same species before being subjected to the pre-treatment step and the germination induction step, plant seeds of the same species subjected to the pre-treatment step but not the germination induction step, or plant seeds of different species known to produce a target substance, plant seeds as a negative control which do not produce the target substance.

EXAMPLES

<Tests Using Grape Seeds>

Example 1

Germinated plant seeds were manufactured using grape seeds (Variety: Cabernet Sauvignon). First, as the pre-treatment, grape seeds (300 g) were placed in a substantially sealed container, and then watering was performed every 8 hours (immersed for 1 minute and then drained over 1 minute), thereby maintaining an atmosphere continuously for 6 hours in which the mean concentration of carbon dioxide was 20000 ppm, and the mean concentration of oxygen was 12 vol %. Watering was performed 21 times in total, and the pre-treatment step was performed for 7 days in total. Note that the water temperature and the room temperature were set to 28° C., and the atmosphere after watering showed an oxygen concentration of 20 vol % and a carbon dioxide concentration of 300 to 390 ppm. By using the pre-treatment described above, the raw material seeds for germination induction according to Example 1 were manufactured.

Germination induction was performed after inoculating the raw material seeds for germination induction according to Example 1 which had been subjected to the pre-treatment with yeast (Variety: Saccharomyces cerevisiae). Inoculation was performed with California wine yeast RP15 Starter. After inoculation, the yeast was allowed to grow for 6 days while performing germination induction under an environment of an oxygen concentration of 8 vol % and a carbon dioxide concentration of 20000 ppm at 24° C. The germinated plant seeds according to Example 1 were manufactured as described above.

Resveratrol and resveratrol glycoside (piceid), which are phytoalexin, in the germinated plant seeds according to Example 1 were quantified. First, ethanol and water were added to achieve 10-times dilution relative to the mass of the germinated plant seeds according to Example 1, and ground for 1 second into 0.5 mm or less. A solution containing the grape seeds after grinding was measured into a 15 ml centrifuge tube, and sonicated for 20 minutes to prepare an extract composition. Subsequently, compounds in the composition were analyzed using this extract composition. Analysis was performed under the following conditions.

Column: AQCUITY UPLC BEH Shield RP18 Column (1.7 μm, 2.1 mm.×150 mm), AQCUITY UPLC BEH Shield RP18 VanGuard Pre-Column (1.7 μm, 2.1 mm.×5 mm)/Column temperature: 35° C./water (0.1% acetic acid), ACN (0.1% acetic acid): 0 to 10 min 15%, 10 to 55 min 100%, 55 to 60 min 100%, 60 to 70 min 15%

Comparative Example 1

Those similar to the grape seeds before performing the pre-treatment and the germination treatment according to Example 1 were prepared to produce an extract composition thereof as in Example 1, and then compounds in the composition were analyzed.
(Analysis Result 1)

Figure 1B:
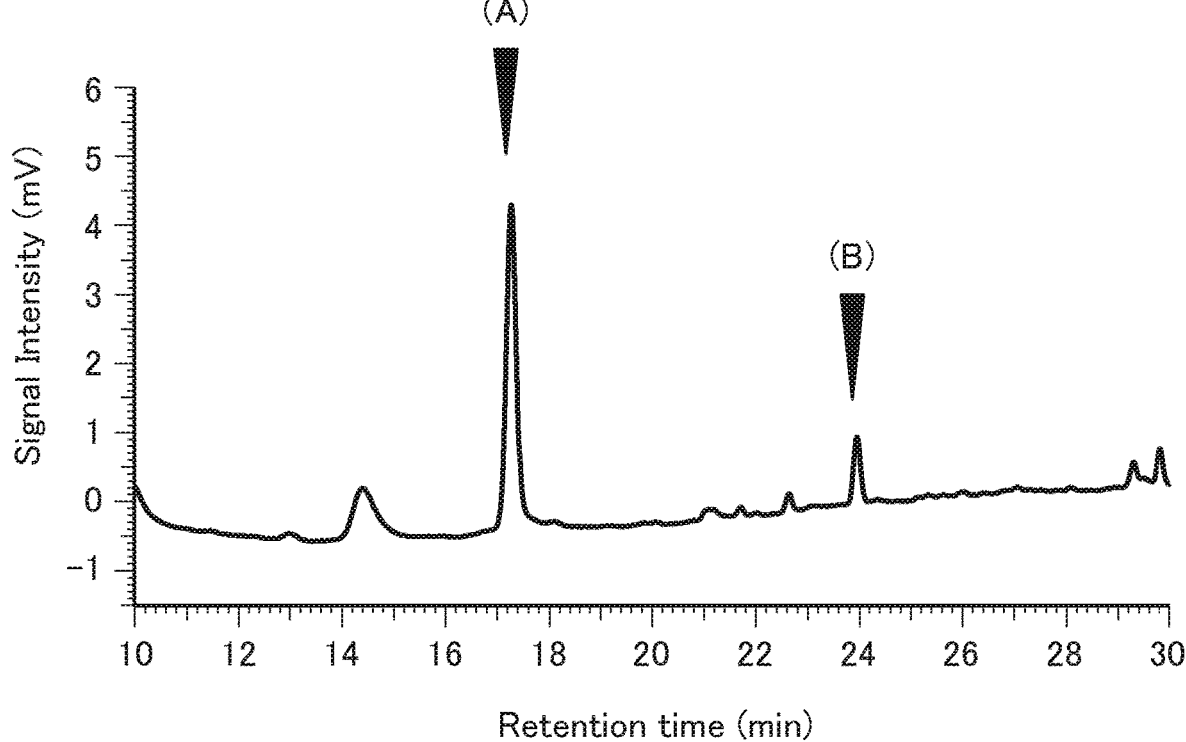

Results from each analysis of Example 1 and Comparative Example 1 are shown in FIG. 1. The peak indicated by the arrow (A) in FIG. 1 represents piceid, and the peak indicated by the arrow (B) represents resveratrol. As shown in FIG. 1, the germinated plant seeds according to Example 1 were found to contain piceid and resveratrol in significantly larger quantities as compared with the grape seeds according to Comparative Example 1. Further, the amount of a phytochemical in the grape seeds according to Comparative Example 1 (the grape seeds before the pre-treatment) is 10 mg/g while the amount of the phytochemical in the raw material seeds for germination induction according to Example 1 (the raw material seeds for germination induction after the pre-treatment) was 25 mg/g. Further, the amount of phytoalexin produced in the germinated plant seeds according to Example 1 was 10 mg/g.

<Tests Using Red Clover Seeds>

Example 2

Raw material seeds for germination induction were manufactured under similar conditions as in Example 1 except that red clover seeds were used as plant seeds, and the pre-treatment was performed for 2 days.

Germination induction was performed after inoculating the raw material seeds for germination induction after the pre-treatment according to Example 2 with an Koji mold (Variety: Aspergillus oryzae). Inoculation was performed with a seed malt (Akita Imano Co., Ltd.). After inoculation, the Koji mold was allowed to grow for 5 days while performing germination induction under the environment of an oxygen concentration of 8 vol % and a carbon dioxide concentration of 20000 ppm at 24° C. The germinated plant seeds according to Example 2 were manufactured as described above.

Various types of isoflavone as phytoalexin in the germinated plant seeds according to Example 2 were analyzed. An extract composition was prepared according to the procedures similar to those in Example 1. Analysis was performed under the following conditions.

Column: AQCUITY UPLC BEH Shield RP18 Column (1.7 μm, 2.1 mm.×150 mm), AQCUITY UPLC BEH Shield RP18 VanGuard Pre-Column (1.7 μm, 2.1 mm.×5 mm)/Column temperature: 35° C./water (0.1% acetic acid), ACN (0.1% acetic acid): 0 to 2 min 15 to 20%, 2 to 5 min 25%, 5 to 6 min 30%, 6 to 8 min 40%, 8 to 9 min 45%, 9 to 10 min 45%, 10 to 12 min 50%, 12 to 22 min 100%, 22 to 24 min 100%, 24 to 25 min 15%, 25 to 27 min 15%

Example 3

Manufacture of raw material seeds for germination induction, manufacture of germinated plant seeds and quantification of isoflavone were all performed under similar conditions as in Example 2 except that the pre-treatment was performed for 4 days. Note that the amount of a phytochemical in the red clover seeds before the pre-treatment was 5 mg/g while the amount of the phytochemical in the raw material seeds for germination induction after the pre-treatment was 40 mg/g.

Comparative Example 2

Those similar to the red clover seeds before performing the pre-treatment and the germination treatment in Example 2 (the seeds according to Comparative Example 2) were prepared to produce an extract composition thereof as in Example 2, and compounds in the composition were analyzed.
(Analysis Result 2)

Figure 2A:
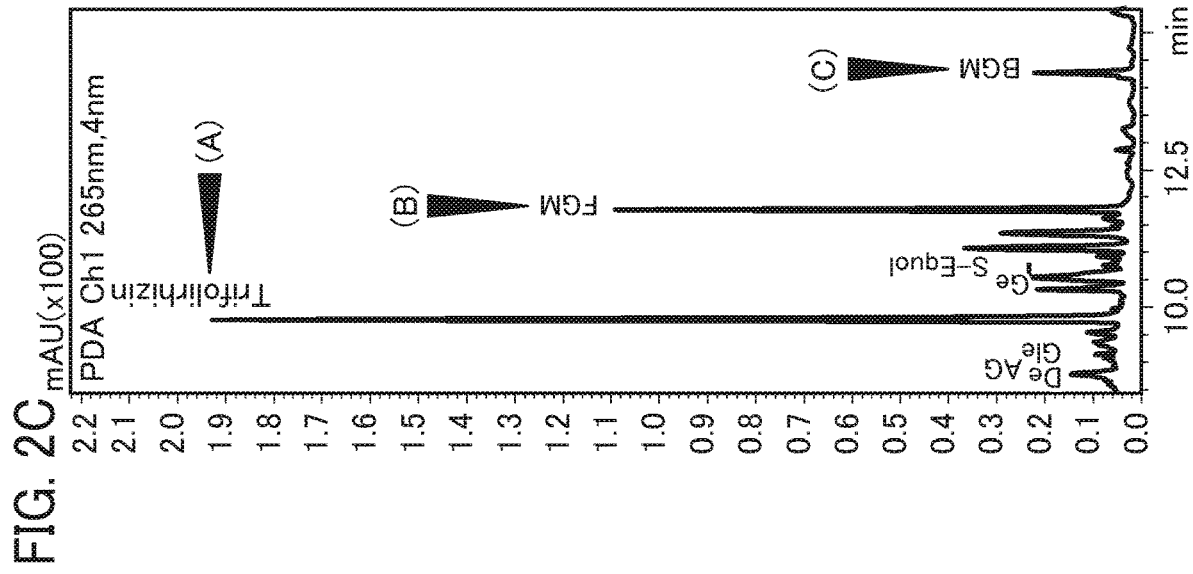
FIG. 2 shows analysis results from high performance liquid chromatography of (FIG. 2A) an extract composition of the red clover seeds according to Comparative Example 2, (FIG. 2B) an extract composition of the germinated plant seeds according to Example 2 and (FIG. 2C) an extract composition of the germinated plant seeds according to Example 3.
Figure 2B:
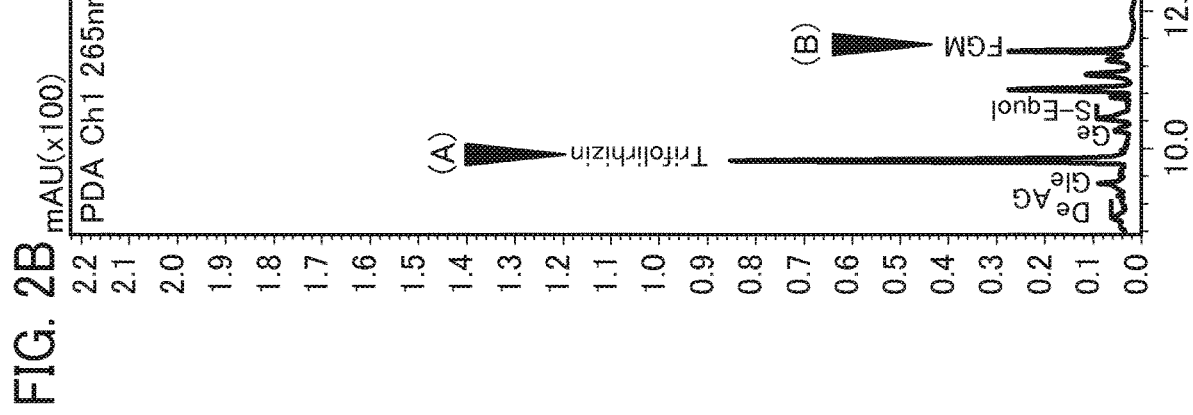
Figure 2C:
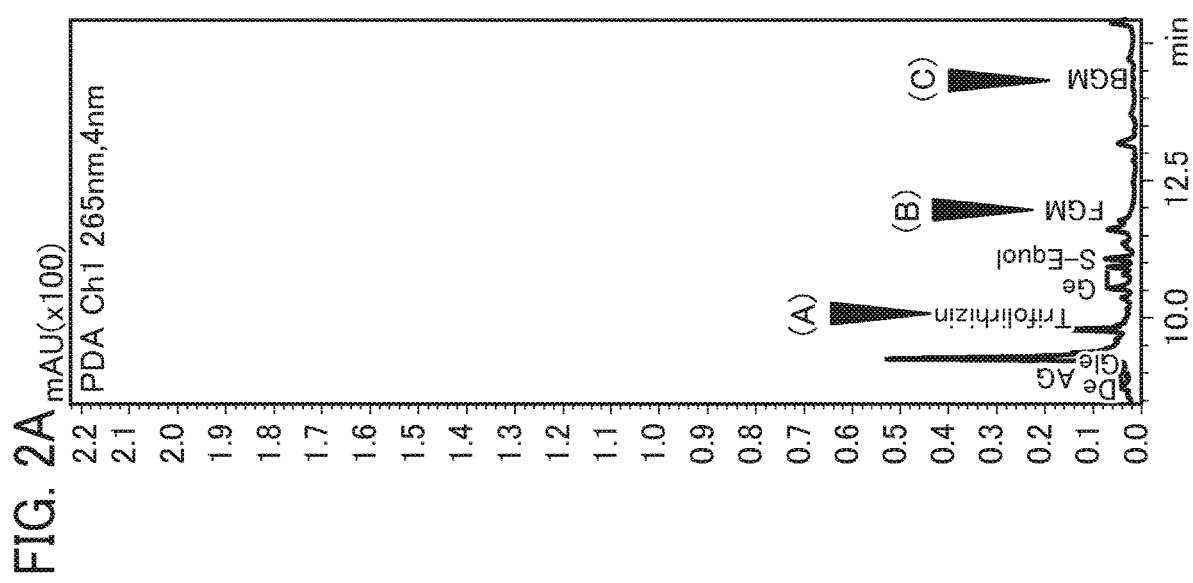

Results from each analysis of Examples 2 and 3 and Comparative Example 3 are shown in FIG. 2. In FIG. 2, the peak indicated by the arrow (A) represents trifolirhizin, and the peak indicated by the arrow (B) represents formononetin (Formononetin glucoside Malonate), and the peak indicated by the arrow (C) represents Biochanin A (Biochanin A glucoside Malonate). Further, the area ratios of each peak area for trifolirhizin, formononetin and Biochanin A are shown in Table 1 below.

TABLE 1

| | Sample | | |
|---|---|---|---|
| Compound | Comparative Example 2 | Example 2 | Example 3 |
| Trifolirhizin | 73,345(8%) | 403,027(47%) | 865,862(100%) |
| Formononetin | 27,218(6%) | 115,428(27%) | 420,822(100%) |
| Biochanin A | 2,579(3%) | 39,649(43%) | 92,768(100%) |

As shown in FIG. 2 and Table 1, the amounts of trifolirhizin and formononetin were found to be increased in the germinated plant seeds according to Examples 2 and 3 as compared with those in the seeds without any treatment according to Comparative Example 2. In particular, trifolirhizin, formononetin and Biochanin A were found to be increased by 11.80 times, 15.46 times and 35.90 times, respectively in the germinated plant seeds according to Example 3 which were subjected to the pre-treatment for 4 days as compared with those in the seeds according to Comparative Example 2. Note that the amount of a phytochemical in the red clover seeds (the red clover seeds before the pre-treatment) according to Comparative Example 2 was 5 mg/g while the amount of the phytochemical in the raw material seeds for germination induction according to Example 2 (the raw material seeds for germination induction after the pre-treatment) was 20 mg/g. Further, the amount of a phytochemical in the raw material seeds for germination induction according to Example 3 (the raw material seeds for germination induction after the pre-treatment) was 40 mg/g as described above, and the amount of phytoalexin produced in the germinated plant seeds according to Example 3 was 30 mg/g.

<Tests Using Tomato Seeds>

Example 4

Raw material seeds for germination induction were manufactured under similar conditions as in Example 1 except that tomato (Variety: red pair) seeds were used.

An extract composition of the germinated plant seeds according to Example 4 was prepared, and phytochemicals were analyzed. Analysis was performed under the following conditions.

Analytical instrument: Hitachi high performance liquid chromatograph (HPLC)/Detector: UV detector/Column: GL Sciences ODS (6.0 mm I.D.×150 mm)/Column temperature: 35° C./water (0.1% acetic acid), ACN (0.1% acetic acid): 0 to 10 min 15%, 10 to 55 min 100%, 55 to 60 min 100%, 60 to 70 min 15%

Comparative Example 3

Those similar to the tomato seeds before performing the pre-treatment in Example 4 were prepared, and used to produce an extract composition as in Example 4, and phytochemicals in the composition were analyzed under similar conditions as in Example 4.

(Analysis Result 3)

Figure 3A:
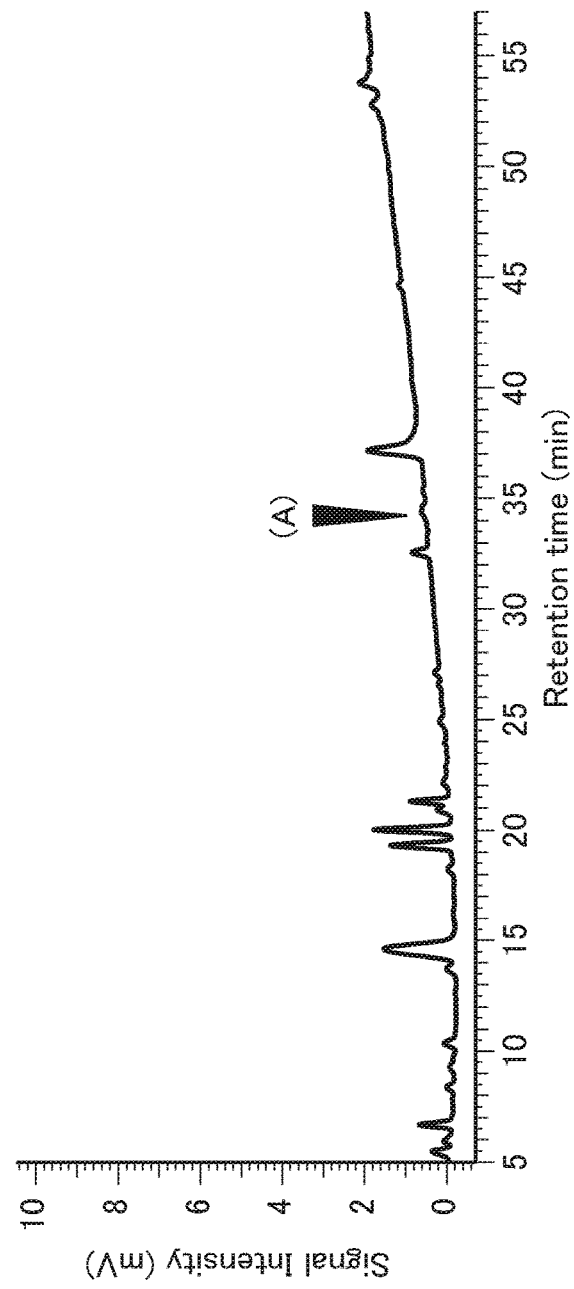
FIG. 3 shows analysis results from high performance liquid chromatography of (FIG. 3A) an extract composition of the tomato seeds according to Comparative Example 3 and (FIG. 3B) an extract composition of the raw material seeds for germination induction according to Example 4.
Figure 3B:
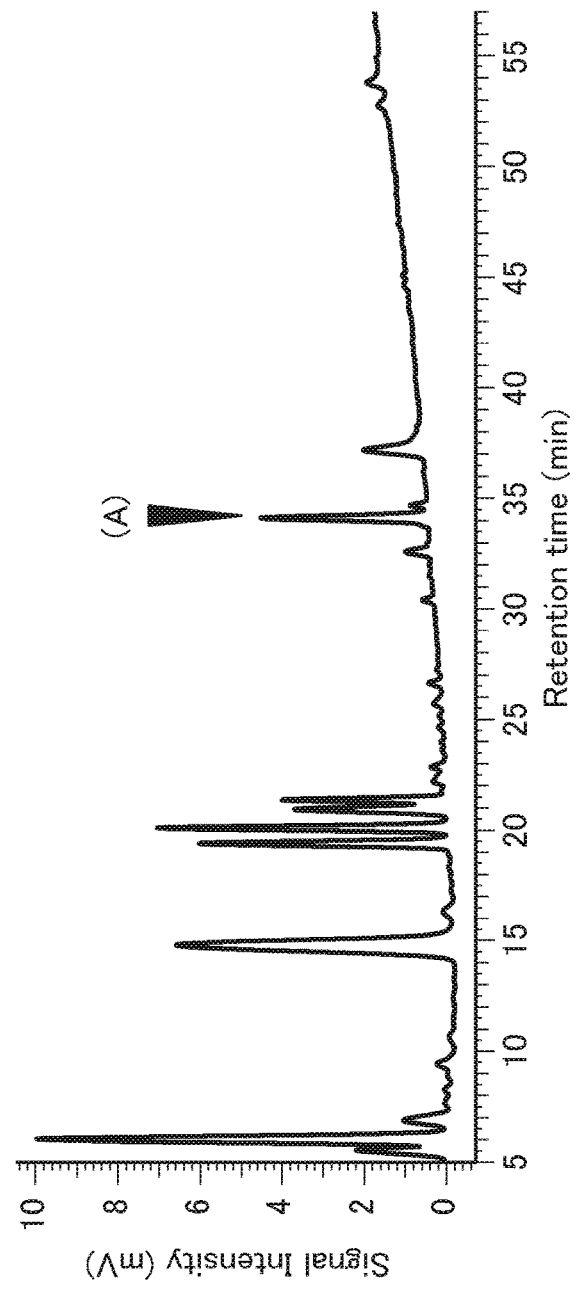

Results from each analysis of Example 4 and Comparative Example 3 are shown in FIG. 3. As shown in FIG. 3, the amounts of phytochemicals were found to be changed. Specifically, among phytochemicals, naringenin chalcone in particular was found to be increased. The peak indicated by the arrow (A) in FIG. 3 represents naringenin chalcone. Further, the amount of a phytochemical in the tomato seeds according to Comparative Example 3 (the tomato seeds before the pre-treatment) was 4 mg/g while the amount of the phytochemical in the raw material seeds for germination induction according to Example 4 was 16 mg/g.

<Tests Using Soybean>

Example 5

Raw material seeds for germination induction were manufactured by performing the pre-treatment step under similar conditions as in Example 1 except that soybean (Variety: Ohtsuru) was used as plant seeds, and the atmosphere during the maintenance was such that the concentrations of oxygen and carbon dioxide were 10 vol % and 40000 ppm, respectively and the pre-treatment was carried out for 1 day.

The raw material seeds for germination induction according to Example 5 were ground, and an extract composition was prepared to analyze isoflavone as a phytochemical. Analysis was performed under the following conditions.

Analytical instrument: Shimazu high performance liquid chromatograph (UHPLC)/Detector: Photodiode array detector/Column: Shim-pack XR-ODSIII/(2.0 mm I.D.×150 mm)/Column temperature: 35° C./water (0.1% acetic acid), ACN (0.1% acetic acid): 0 to 2 min 15 to 20%, 2 to 5 min 25%, 5 to 6 min 30%, 6 to 8 min 40%, 8 to 9 min 45%, 9 to 10 min 45%, 10 to 12 min 50%, 12 to 22 min 100%, 22 to 24 min 100%, 24 to 25 min 15%, 25 to 27 min 15%

Example 6

Raw material seeds for germination induction were manufactured under similar conditions as in Example 5 except that Akita-midori was used as a variety of soybean.

The raw material seeds for germination induction according to Example 6 were ground, and an extract composition was prepared to analyze isoflavone as a phytochemical under similar conditions as in Example 5.

Example 7

Raw material seeds for germination induction were manufactured under similar conditions as in Example 5 except that Kurosengoku was used as a variety of soybean.

The raw material seeds for germination induction according to Example 7 were ground, and an extract composition was prepared to analyze isoflavone as a phytochemical under similar conditions as in Example 5.

Comparative Example 4

Those similar to the soybean (Variety: Ohtsuru) before performing the pre-treatment in Example 5 were prepared, and were used to produce an extract composition as in Example 5, and isoflavone as a phytochemical in the composition was analyzed under similar conditions as in Example 5.

Comparative Example 5

Those similar to the soybean (Variety: Akita-midori) before performing the pre-treatment in Example 6 were prepared, and were used to produce an extract composition as in Example 6, and isoflavone as a phytochemical in the composition was analyzed under similar conditions as in Example 5.

Comparative Example 6

Those similar to the soybean (Variety: Kurosengoku) before performing the pre-treatment in Example 7 were prepared, and were used to produce an extract composition as in Example 7, and isoflavone as a phytochemical in the composition was analyzed under similar conditions as in Example 5.

Comparative Example 7

An extract composition was prepared under similar conditions as in Example 5 except that the concentrations of oxygen and carbon dioxide were 20 vol % and 390 ppm, respectively during the maintenance in Example 5, and isoflavone as a phytochemical in the composition was analyzed under similar conditions as in Example 5.

Comparative Example 8

An extract composition was prepared under similar conditions as in Example 6 except that the concentrations of oxygen and carbon dioxide were 20 vol % and 390 ppm, respectively during the maintenance in Example 6, and isoflavone as a phytochemical in the composition was analyzed under similar conditions as in Example 5.

Comparative Example 9

An extract composition was prepared under similar conditions as in Example 7 except that the concentrations of oxygen and carbon dioxide were 20 vol % and 390 ppm, respectively during the maintenance in Example 7, and isoflavone as a phytochemical in the composition was analyzed under similar conditions as in Example 5.
(Analysis Result 4)

Figure 4:
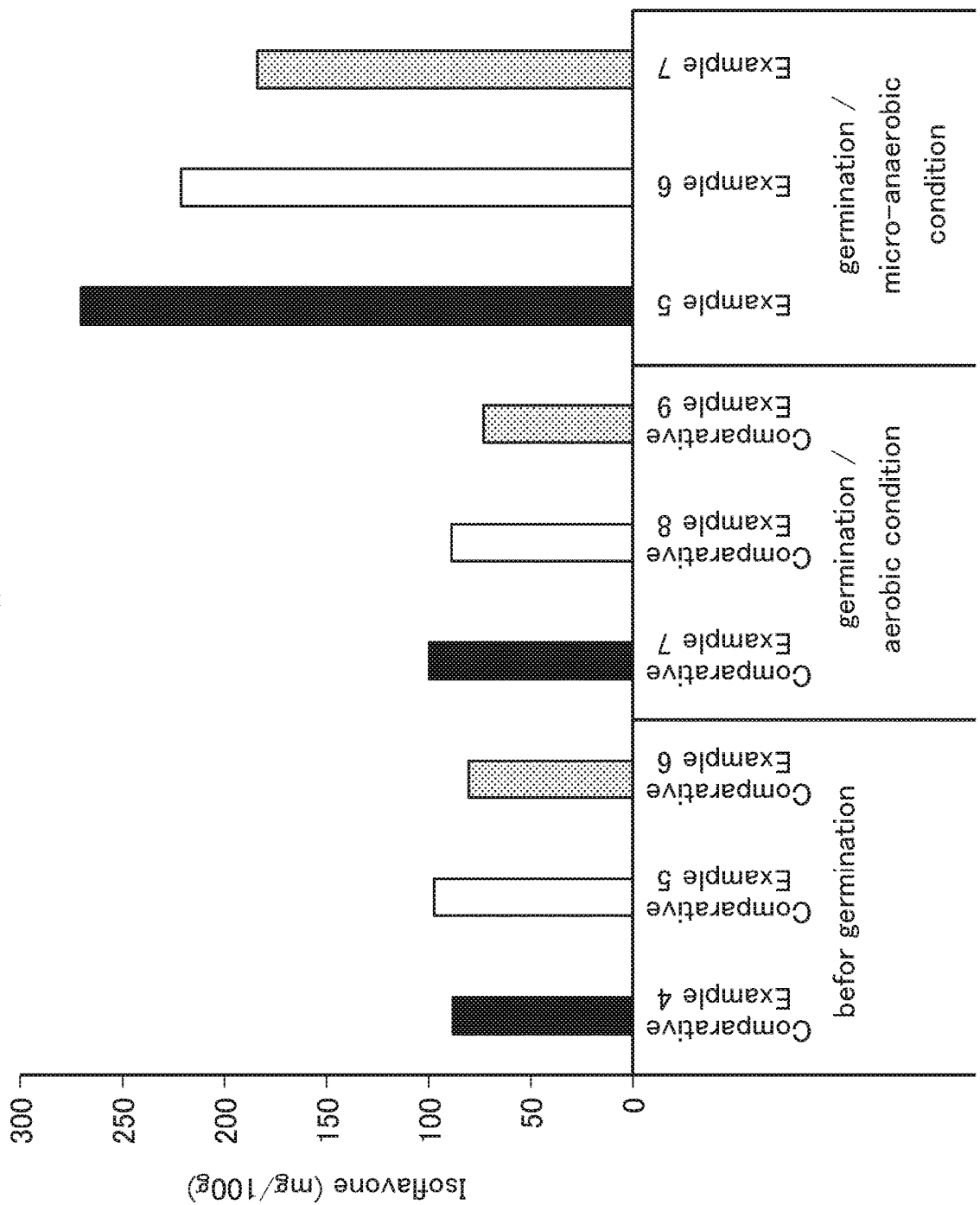
FIG. 4 shows a graph illustrating the amounts of isoflavone as a phytochemical in the compositions extracted from the raw material seeds for germination induction according to Examples 5 to 7 and from the soybean according to Comparative Examples 4 to 9.

The amounts of isoflavone as a phytochemical for Examples 5 to 7 and Comparative Examples 4 to 9 are shown in FIG. 4. In FIG. 4, "before germination" corresponds to the seeds without any germination inducing treatment (the soybeans according to Comparative Examples 4 to 6), and "germination/aerobic condition" corresponds to the seeds subjected to the germination inducing treatment under aerobic conditions (the soybeans according to Comparative Examples 7 to 9), and "germination/micro-anaerobic condition" corresponds to the seeds subjected to the germination inducing treatment under anaerobic conditions (the raw material seeds for germination induction according to Examples 5 to 7). As shown in FIG. 4, the amounts of isoflavone as a phytochemical in the raw material seeds for germination induction according to Examples 5 to 7 were 2.8 to 3.0 times higher than those in the soybeans without any treatment according to Comparative Examples 4 to 6, and those in the soybeans treated under the aerobic atmosphere conditions of an oxygen volume of 20% according to Comparative Examples 7 to 9. The results also support that the amount of a phytochemical in plant seeds is increased by the pre-treatment according to the present invention.

Further, the amounts of various types of isoflavone as a phytochemical contained in the raw material seeds for germination induction according to Examples 5 to 7 and in the soybeans according to Comparative Examples 4 to 9 are shown in FIG. 5. In FIG. 5, (FIG. 5A) shows a graph of the amounts of various types of isoflavone as a phytochemical in the extract compositions of the soybeans according to Comparative Examples 4 to 6, and (FIG. 5B) shows a graph of the amounts of various types of isoflavone as a phytochemical in the extract compositions of the soybeans according to Comparative Examples 7 to 9, and (FIG. 5C) shows a graph of the amounts of various types isoflavone as a phytochemical in the extract compositions of the raw material seeds for germination induction according to Examples 5 to 7. As shown in FIG. 5, the raw material seeds for germination induction according to Examples 5 to 7 were found to contain, in particular, malonyl-genistin and malonyl-daidzin in significantly higher amounts as compared with the soybeans according to Comparative Examples 4 to 9.

Example 8

Raw material seeds for germination induction were manufactured by performing the pre-treatment step under similar conditions as in Example 1 except that soybean (Variety: Ohtsuru) was used as plant seeds under similar conditions as in Example 5, and the atmosphere during the maintenance was such that the concentrations of oxygen and carbon dioxide were 10 vol % and 40000 ppm, respectively.

The germinated plant seeds according to Example 2 were manufactured using the procedures similar to those in Example 1 except that the raw material seeds for germination induction according to Example 8 were used, and Tempeh fungus (Strain: *Rhizopus* sp.) was used as a pathogen.

Glyceollin in the germinated plant seeds according to Example 8 was analyzed. An extract composition was prepared according to the procedures similar to those in Example 1. The analysis conditions were as follows.

Analytical instrument: Shimazu high performance liquid chromatograph (UHPLC)/Detector: Photodiode array detector/Column: AQCUITY UPLC BEH Shield RP18 Column (1.7 μm, 2.1 mm.×150 mm), AQCUITY UPLC BEH Shield RP18 VanGuard Pre-Column/(1.7 μm, 2.1 mm.×5 mm), Column temperature: 35° C./water (0.1% acetic acid), ACN (0.1% acetic acid): 0 to 2 min 15 to 20%, 2 to 5 min 25%, 5 to 6 min 30%, 6 to 8 min 40%, 8 to 9 min 45%, 9 to 10 min 45%, 10 to 12 min 50%, 12 to 22 min 100%, 22 to 24 min 100%, 24 to 25 min 15%, 25 to 27 min 15%

Example 9

Manufacture of the raw material seeds for germination induction, manufacture of the germinated plant seeds, preparation of an extract composition, and analysis of glyceollin were performed under similar conditions as in Example 8 except that a Koji mold (strain: *Aspergillus* sp) was used as a pathogen.

Example 10

Manufacture of the raw material seeds for germination induction, manufacture of the germinated plant seeds, preparation of an extract composition, and analysis of glyceollin were performed under similar conditions as in Example 8 except that lactic acid bacteria (*Lactobacillus* sp.) was used as a pathogen.

Comparative Example 10

Manufacture of the raw material seeds for germination induction, manufacture of the germinated plant seeds, preparation of an extract composition, and analysis of glyceollin were all performed under similar conditions as in Examples 8 to 10 except that a pathogen was not used.
(Analysis Result 5)

Figure 6:
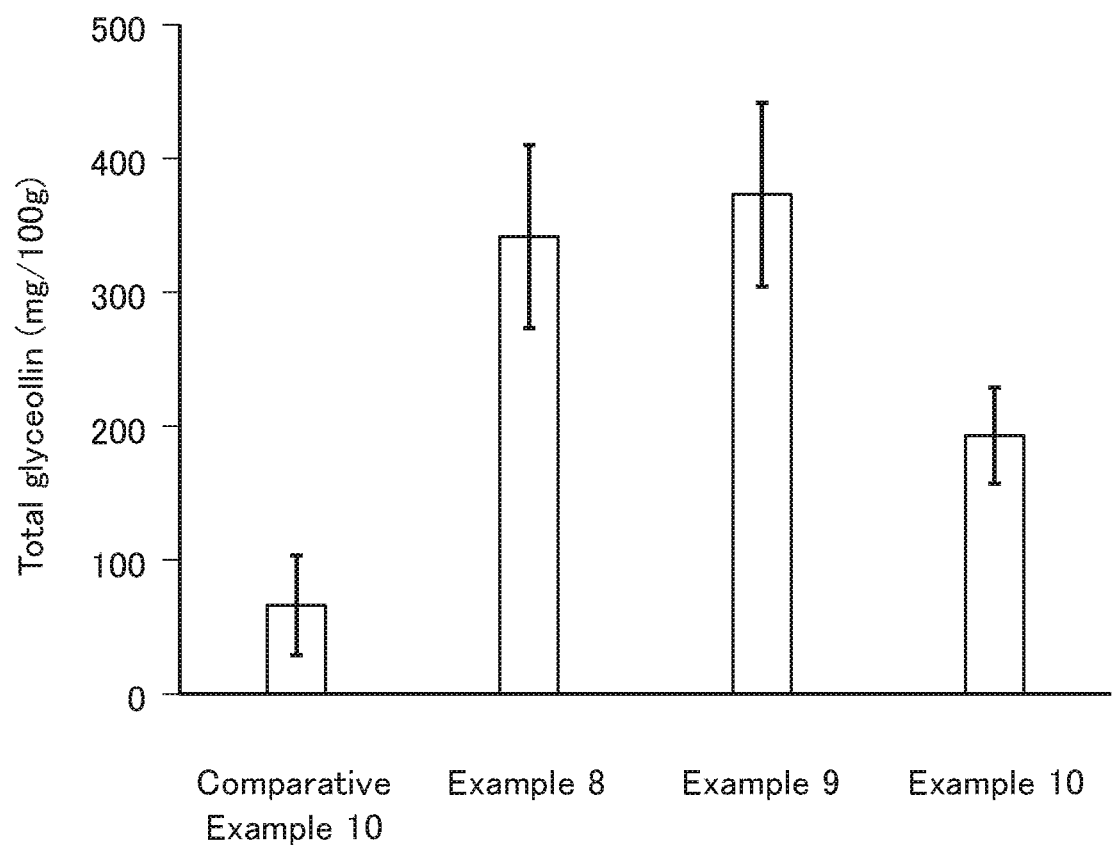
FIG. 6 shows a graph illustrating the amounts of glyceollin as a phytochemical in the compositions extracted from the germinated plant seeds according to Examples 8 to 10 and from the seeds according to Comparative Example 10.

The amounts of glyceollin for Examples 8 to 10 and Comparative Example 10 are shown in FIG. 6. As shown in FIG. 6, the amounts of glyceollin were found to be significantly larger in the germinated plant seeds according to Examples 8 to 10 as compared with those in Comparative Example 10 where inoculation with a pathogen was not performed. Note that the amount of phytoalexin produced in the germinated plant seeds according to Example 8 was 25 mg/g. The amount of phytoalexin produced in the germinated plant seeds according to Example 9 was 25 mg/g. The amount of phytoalexin produced in the germinated plant seeds according to Example 10 was 25 mg/g.

Figure 7:
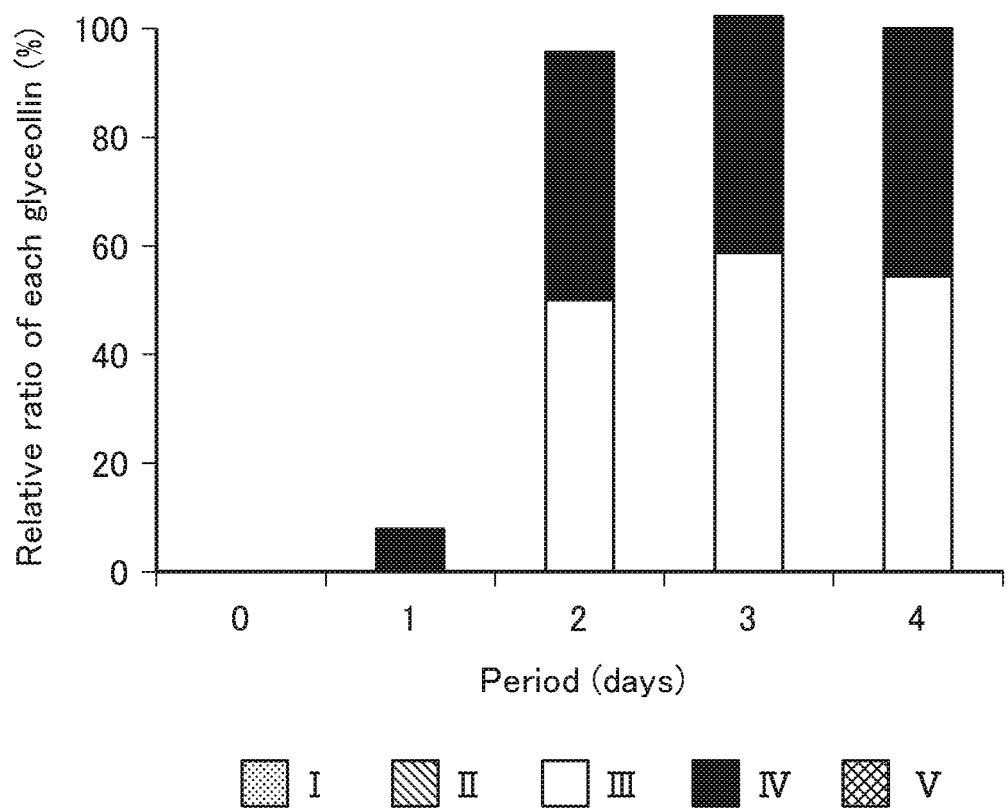
FIG. 7 shows a graph illustrating the relation between the time course after inoculation with Koji mold (Day 0 to Day 4) and the rate of increase in Glyceollins I to V for the germinated plant seeds according to Example 9.

Further, the amounts of Glyceollins I to V that were increased over time after inoculation with the Koji mold (Day 0 to Day 4) was investigated for the germinated plant seeds according to Example 9. The results are shown in FIG. 7. In FIG. 7, "I" to "V" represent "Glyceollins I to V", respectively. Note that one having the largest mass was taken as 100% in FIG. 7. As shown in FIG. 7, Glyceollins III and IV were found to be significantly increased among the Glyceollins. In particular, Glyceollin III is known to have efficacy for suppression of breast cancer, beautiful skin effects and the like. Therefore, the results revealed that not only the amount of glyceollin but also the ratio of useful Glyceollin III were increased by manufacturing germinated plant seeds according to the method of the present invention using soybean as plant seeds.

Example 11

Raw material seeds for germination induction were manufactured under similar conditions as in Example 1 except that soybean (Variety: Ohtsuru) was used as plant seeds.

An extract composition was prepared by grinding the raw material seeds for germination induction according to Example 11, and analyzed for amino acids. The analysis conditions were as follows.

Shimazu high performance liquid chromatograph (UH-PLC)/Detector: Fluorescence detector/Column: YMC Triart C18 1.9 mm (50 mm L.×3.0 mm I.D.)/Column temperature: 35° C./water (0.1% acetic acid), ACN (0.1% acetic acid): 0 to 1.5 min 9.5%, 1.5 to 4.5 min 18.5%, 4.5 to 6.5 min 25%, 6.5 to 8.5 min 45%, 8.5 to 12 min 85%

Comparative Example 11

Seeds similar to the soybean before performing the pre-treatment in Example 11 were prepared and used to produce an extract composition as in Example 11. Amino acids in the composition were analyzed under similar conditions as in Example 11.

Comparative Example 12

An extract composition was prepared under similar conditions as in Example 11 except that the pre-treatment in Example 11 was not performed, and instead, common germination treatment (conditions: under the atmosphere of an oxygen concentration of 20 vol %, a carbon dioxide concentration of 300 ppm and a temperature of 26° C.) was performed. Amino acids in the composition were analyzed under similar conditions as in Example 11.
(Analysis Result 6)

Figure 8:
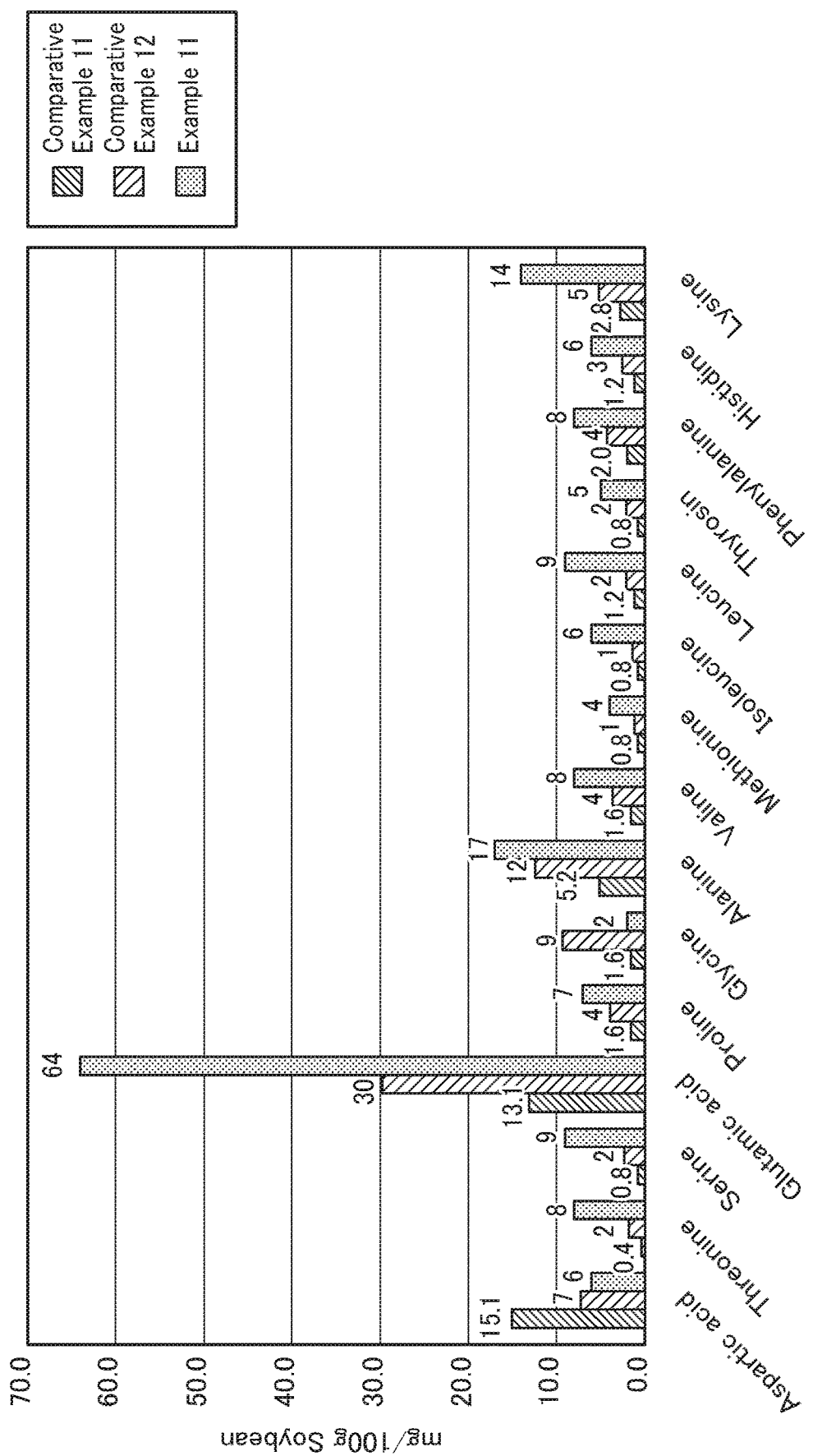
FIG. 8 shows a graph illustrating the amounts of amino acids in the composition extracted from the raw material seeds for germination induction according to Example 11, and from the seeds according to Comparative Examples 11 and 12.

Analysis results of each of Example 11 and Comparative Examples 11 and 12 are shown in FIG. 8. From FIG. 8, the raw material seeds for germination induction according to Example 11 were found to contain a significantly increased amount of amino acids as compared with the soybean according to Comparative Example 11 which was not subjected to any treatment, and the soybean according to Comparative Example 12 which was subjected to the common germination treatment. In particular, the amount of glutamic acid was found to be significantly increased.

The amount of a phytochemical is increased by the pre-treatment according to the present invention. Therefore, a pathogen would be less viable after inoculation. However, since amino acids as nutrients for a pathogen are significantly increased in the seeds by the pre-treatment as described above, the pathogen can be more tolerant to the phytochemical. Therefore, this can be assumed as follows: in Examples in which inoculation was performed with a microbial pathogen, the pathogen could grow in a state where a phytochemical was present in a large amount, during which mutual stimulation occurred between the pathogen and the raw material seeds for germination induction after the pre-treatment. As a result, a large amount of phytoalexin was produced in the seeds.

The invention claimed is:

1. A method of treating plant seeds for germination induction, comprising a pre-treatment step of maintaining the plant seeds under atmosphere conditions of a carbon dioxide concentration of 2000 ppm to 50,000 ppm and an oxygen concentration of 7 vol % to 19 vol % continuously for 5 hours or more, followed by watering,
wherein the plant seeds are those of Vitaceae, Leguminosae, or tomato.

2. The method of treating plant seeds for germination induction according to claim 1, wherein the maintenance for 5 hours or more is not performed by immersing the plant seeds in water.

3. The method of treating plant seeds for germination induction according to claim 1, wherein the pre-treatment comprises performing a combination of the maintenance under said atmosphere conditions for 5 hours or more followed by termination of the maintenance, wherein the combination is repeated 2 or more times more.

4. The method of treating plant seeds for germination induction according to claim 1, wherein the plant seeds comprise phytochemicals and so that the mass of a phytochemical in the plant seeds, after the pre-treatment step, is from 2 times to 100 times relative to the mass of the phytochemical in the plant seeds before the pre-treatment step.

5. The method of treating plant seeds for germination induction according to claim 4, wherein the mass of the entire phytochemicals in the plant seeds after the pre-treatment step is from 2 times to 100 times relative to the mass of the entire phytochemicals in the plant seeds before the pre-treatment step.

6. The method of treating plant seeds for germination induction according to claim 1, wherein the plant seeds comprise glutamic acid and the mass of glutamic acid in the plant seeds after the pre-treatment step is 2.5 times or more relative to the mass of glutamic acid in the plant seeds before the pre-treatment step.

7. The method of treating plant seeds for germination induction according to claim 1, wherein the plant seeds comprise phytochemicals and the phytochemical content in the plant seeds before the pre-treatment step is 0.1 mg/g or more.

8. The method of treating plant seeds for germination induction according to claim 1, wherein the plant seeds are maintained under the atmosphere conditions continuously for 5 hours or more and 72 hours or less.

9. A method of germinating the treated plant seeds according to claim 1, the method comprising a germination induction step of inoculating the treated plant seeds with a microbial pathogen, and placing the treated plant seeds in an environment where germination is inducible and the pathogen is viable.

10. The method of germinating plant seeds according to claim 9, wherein the pathogen is an edible microorganism.

11. A screening method for a plant seed candidate for use in producing a target substance, comprising:
a pre-treatment step of maintaining test plant seeds under atmosphere conditions of a carbon dioxide concentration of 2000 ppm to 50,000 ppm and an oxygen concentration of 7 vol % to 19 vol % continuously for 5 hours or more, followed by watering, a germination induction step of inoculating the test plant seeds with a microbial pathogen after the pre-treatment step, and placing the test plant seeds under an environment in which germination is inducible and the pathogen is viable,
a step of detecting the target substance in the test plant seeds after the germination induction step, and a step of selecting the plant seed candidate for use in producing the target substance based on the detection results.

12. The screening method according to claim 11, wherein the maintenance for 5 hours or more is not performed by immersing the test plant seeds in water.

13. The screening method according to claim 11, wherein the pre-treatment step comprises performing a combination of the maintenance under said atmosphere conditions for 5 hours or more followed by termination of the maintenance, wherein the combination is repeated 2 or more times.

14. The screening method according to claim 11, wherein the test plant seeds comprise phytochemicals and the mass of the entire phytochemicals in the test plant seeds after the pre-treatment step is from 2 times to 100 times relative to the mass of the entire phytochemicals in the test plant seeds before the pre-treatment step.

15. The screening method according to claim 11, wherein the test plant seeds comprise glutamic acid and the mass of glutamic acid in the test plant seeds after the pre-treatment step is 2.5 times or more relative to the mass of glutamic acid in the test plant seeds before the pre-treatment step.

* * * * *